April 19, 1955 E. S. BOERNER Plant Pat. 1,380
ROSE PLANT
Filed July 6, 1954
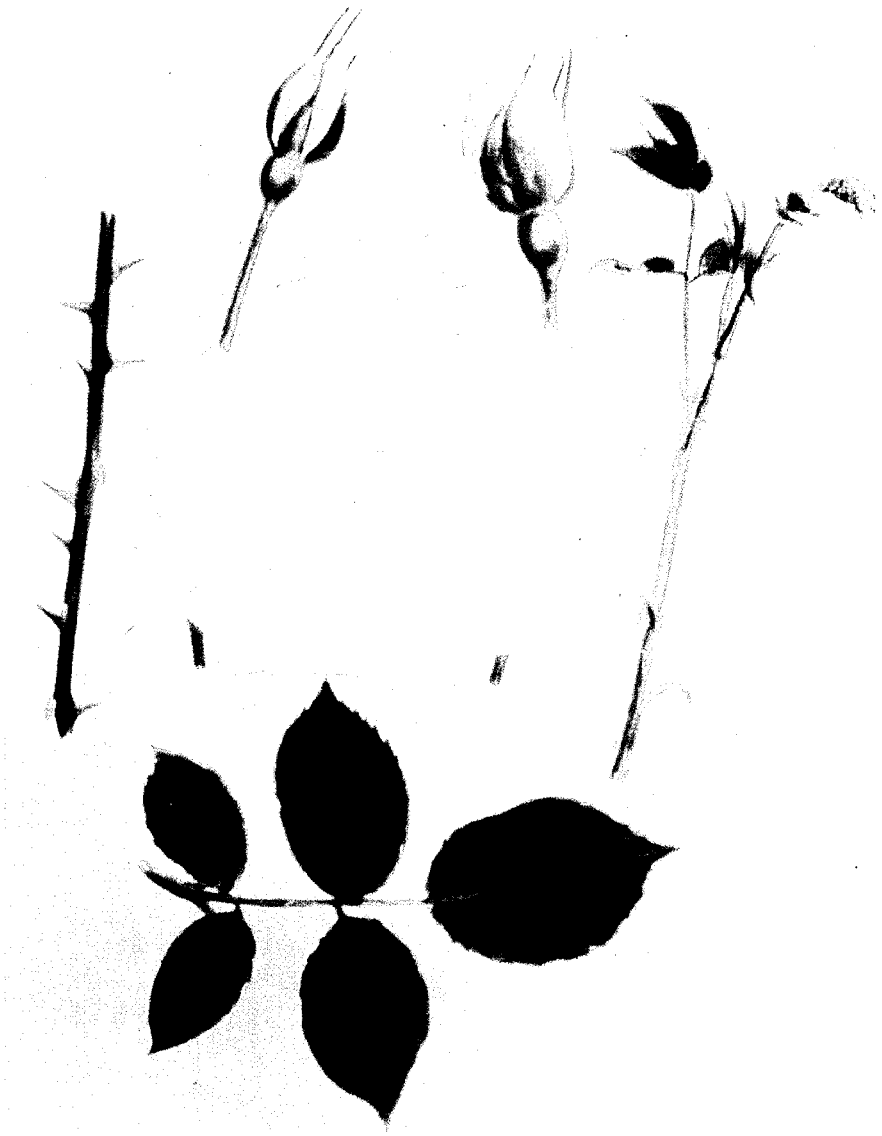
Inventor.
E. S. Boerner
By. Robb & Robb
Attorneys.

United States Patent Office

Plant Pat. 1,380
Patented Apr. 19, 1955

1,380

ROSE PLANT

Eugene S. Boerner, Newark, N. Y., assignor to Jackson & Perkins Company, Newark, N. Y., a corporation of New York Application July 6, 1954, Serial No. 441,699

1 Claim. (Cl. 47—61)

The present invention relates to a new and distinct variety of rose plant of the large-flowered polyantha class, which was originated by me as a self-seedling of an unnamed and unpatented semi-single yellow floribunda variety derived by crossing an unnamed and unpatented climbing seedling with the variety "Golden Main" (Pl. Pat. #254).

The primary objective which I have sought to achieve was to produce a new yellow-flowered floribunda variety of good petalage, combined with a good, healthy plant. This objective was fully attained, as evidenced by the fact that the new variety is particularly characterized as to novelty by the clear, long-lasting yellow blooms which are borne on healthy, vigorous, upright plants. In addition to these primary characteristics, the new variety is still further noted for its slender buds which open to cup-shaped flowers, and for the long, decorative thorns on the wood which contribute to the attractiveness of the plants. All of these characteristics, taken together, represent a unique and distinctive combination in roses of this class, and definitely differentiate the new variety from its parents, as well as from all other varieties of which I am aware.

Asexual reproduction of the new variety by budding at Newark, New York, and also at Pleasanton, California, shows that the foregoing characteristics and distinctions come true to form and are established and transmitted through succeeding propagations.

The accompanying drawing shows typical specimens of the foliage, stems and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling. A self-seedling of an unnamed, semi-single yellow floribunda.
Classification:
*Botanic.*—Large-flowered polyantha.
*Commercial.*—Floribunda.

FLOWER (Observations made from specimens grown in a greenhouse at Newark, New York, in the early part of the month of April, and in the early morning.)

Blooming habit: Recurrent—continuous.
Bud:
*Size.*—Medium.
*Form.*—Ovoid; pointed; is not affected by wet or hot weather.
*Color.*—When sepals first divide—Lemon Yellow, Plate 4. When petals begin to unfurl—Light Greenish Yellow, Plate 5, lightly overcast with Light Cadmium, Plate 4. When half blown: Inside of petals—Light Cadmium, Plate 4; reverse of petals—Lemon Chrome, Plate 4, lightly overcast with Empire Yellow, Plate 4.
*Sepals.*—Branched; curl back when petals begin to unfurl. Color: Inside—Kildare Green, Plate 31; outside—Light Cress Green, Plate 31.
*Calyx.*—Shape—apple. Size—small. Aspect—smooth. Color—Lettuce Green, Plate 5. Odor when rubbed—none.

*Peduncle.* — Length — medium. Aspect—smooth. Strength—erect; slender. Color—Lettuce Green, Plate 5.
*Opening.*—Opens up well; is not affected by adverse weather conditions.
Bloom:
*Size.*—Medium. Average size when fully expanded—from 3½ inches to 4 inches.
*Borne.*—Several together.
*Stems.*—Medium length; normal strength.
*Form (when first open).*—Cupped. Permanence: All petals curl quill-fashion like a cactus dahlia.
*Petalage.*—Double (full but open center); from 45 to 50 petals under normal conditions.
*Color.*—Center of flower—Empire Yellow, Plate 4. Outer petals—Pinard Yellow, Plate 4. Base of petals (aiglet)—Lemon Chrome, Plate 4. Inside of petals—Empire Yellow, Plate 4, lightly overcast with Pinard Yellow, Plate 4. Reverse of petals—Pinard Yellow, Plate 4. General tonality from a distance—Empire Yellow, Plate 4.
*Discoloration.*—General tonality at end of first day—Empire Yellow, Plate 4. Second day—Empire Yellow, Plate 4, lightly overcast with Pinard Yellow, Plate 4. Third day—Pinard Yellow, Plate 4.
Petals:
*Texture.*—Leathery; is not affected by wet or hot weather.
*Appearance.*—Inside—satiny; outside—shiny.
*Form.*—Oval.
*Arrangement.*—Informal (with "rags" in center).
*Petaloids in center.*—Few; small.
*Persistence.*—Drop off cleanly.
*Fragrance.*—Moderate. Nature—tea (average hybrid tea scent).
*Lasting quality.*—On the plant—long; as cut flower—long.

GENITAL ORGANS

Stamens, anthers: Medium size; many; mixed with petaloids. Color—Buff Yellow, Plate 4.
Stamens, filaments (threads): Medium length. Color—Strawberry Pink, Plate 2.
Pollen: Color—Maize Yellow, Plate 4.
Styles: Bunched; uneven length; short; thin.
Stigmas: Color—pale Orange Yellow, Plate 3.
Ovaries: All enclosed in calyx.
Hips: None.
Seeds: None.

PLANT

Form: Bush.
Growth: Vigorous; upright.
Foliage: 5 to 7 leaflets.
*Size.*—Medium.
*Quantity.*—Normal.
*Color.*—New foliage: Upper side—Lettuce Green, Plate 5, with serrations of Oxblood Red, Plate 1; under side—Courge Green, Plate 17, lightly overcast with Nopal Red, Plate 1. Old foliage: Upper side—Varley's Green, Plate 18; under side—light Bice Green, Plate 17.
*Shape.*—Oval pointed.
*Texture.*—Upper side—glossy; under side—smooth.
*Ribs and veins.*—Ordinary.
*Edge.*—Serrated (saw-toothed).
*Serration.*—Both double and single; small.
*Leaf stem.*—Color—Oil Green, Plate 5. Under side—prickles.
*Stipules.*—Medium length; slightly bearded.
Wood:
*New wood.*—Color—yellowish Oil Green, Plate 5. Bark—smooth.
*Old wood.*—Color—Spinach Green, Plate 5. Bark—smooth.
Thorns:
*Thorns.*—Quantity: On main stalks from base—ordinary; on laterals from stalk—ordinary. Form—narrow base; long; some straight and some hooked downward. Color (when young)—Old Rose, Plate 13. Position—irregular.

*Prickles.*—Quantity: On main stalks—none; on laterals—none.

*Short needles.*—Quantity: On main stalks—none; on laterals—none.

I claim:

A new and distinct variety of rose plant of the large-flowered polyantha class, substantially as herein shown and described, characterized particularly as to novelty by the clear, long-lasting, yellow general color tonality of its flowers, its slender buds and their habit of opening to cup-shaped flowers, its vigorous and healthy plants, and the long, decorative thorns on the wood thereof.

No references cited.